US010783799B1

(12) United States Patent
Horowitz et al.

(10) Patent No.: US 10,783,799 B1
(45) Date of Patent: Sep. 22, 2020

(54) SYSTEM, APPARATUS, AND METHOD FOR EDUCATING AND REDUCING STRESS FOR PATIENTS WITH ILLNESS OR TRAUMA USING AN INTERACTIVE LOCATION-AWARE TOY AND A DISTRIBUTED SENSOR NETWORK

(71) Applicant: SPROUTEL, INC., Providence, RI (US)

(72) Inventors: Aaron J. Horowitz, Providence, RI (US); Joel B. Schwartz, Los Angeles, CA (US); Hannah Chung, Providence, RI (US); Brian Oley, Jamaica Plain, MA (US)

(73) Assignee: Sproutel, Inc., Providence, RI (US)

( * ) Notice: Subject to any disclaimer, the term of this patent is extended or adjusted under 35 U.S.C. 154(b) by 362 days.

(21) Appl. No.: 15/844,537

(22) Filed: Dec. 16, 2017

Related U.S. Application Data

(60) Provisional application No. 62/435,733, filed on Dec. 17, 2016.

(51) Int. Cl.
G09B 5/06 (2006.01)
H04L 29/08 (2006.01)
(Continued)

(52) U.S. Cl.
CPC .............. G09B 5/06 (2013.01); G06F 3/0487 (2013.01); G06F 16/487 (2019.01);
(Continued)

(58) Field of Classification Search
USPC ......................................................... 434/236
See application file for complete search history.

(56) References Cited

U.S. PATENT DOCUMENTS 4,917,607 A * 4/1990 Van Hoose ............ A63H 3/003
434/236
5,405,266 A * 4/1995 Frank ..................... G09B 19/00
434/236
(Continued)

FOREIGN PATENT DOCUMENTS

CN          104952287       3/2014
GB          2508347 A       6/2014
(Continued)

OTHER PUBLICATIONS

A Talking Teddy Bear Practicing in the Pediatric Hospital, Jun. 3, 2015; https://www.nytimes.com/2015/06/04/technology/huggable-robot-therapeutic-value-hospitals.html.
(Continued)

Primary Examiner — Jerry-Daryl Fletcher
Assistant Examiner — Daniel E Lane
(74) Attorney, Agent, or Firm — Renaissance IP Law Group, LLP; David A. Crowther

(57) ABSTRACT

A system, apparatus, and method for educating and reducing stress for patients with childhood illnesses or trauma is disclosed, which uses an interactive location-aware toy and a distributed sensor network in a healthcare facility. Patients are educated and calmed by providing location-specific education and stress reduction techniques. The system's implementation logic can be used to coordinate care for patients, track a patient's progress in completing a custom care treatment plan, and create reminders about appointments, medication adherence, or the like. Healthcare providers can better assist and track the progress of the patient's completion of the custom care treatment plan.

15 Claims, 5 Drawing Sheets

(51) Int. Cl.
  *G09B 19/00* (2006.01)
  *G06F 3/0487* (2013.01)
  *G06F 16/487* (2019.01)

(52) U.S. Cl.
  CPC ........ *G09B 19/0007* (2013.01); *H04L 67/125* (2013.01); *A63H 2200/00* (2013.01); *H04L 67/10* (2013.01)

(56) References Cited

U.S. PATENT DOCUMENTS

| | | | |
|---|---|---|---|
| 5,815,114 A * | 9/1998 | Speasl | G01S 19/11 342/357.48 |
| 6,761,637 B2 | 7/2004 | Weston et al. | |
| 7,967,657 B2 | 6/2011 | Ganz | |
| 8,475,275 B2 | 7/2013 | Weston et al. | |
| 8,500,511 B2 | 8/2013 | Ganz | |
| 8,690,325 B1 * | 4/2014 | Straus | A61B 5/1171 351/200 |
| D714,884 S | 10/2014 | Horowitz et al. | |
| 9,126,122 B2 | 9/2015 | Boeckle | |
| 9,323,323 B2 | 4/2016 | Aleksiev et al. | |
| 9,352,213 B2 | 5/2016 | Yim et al. | |
| 9,390,626 B1 | 7/2016 | Horowitz et al. | |
| 9,480,929 B2 | 11/2016 | Weston | |
| 9,569,562 B2 | 2/2017 | Bulaj et al. | |
| 2004/0161732 A1 * | 8/2004 | Stump | G09B 23/28 434/262 |
| 2004/0197764 A1 * | 10/2004 | Stump | G09B 23/28 434/433 |
| 2006/0234602 A1 * | 10/2006 | Palmquist | A63H 3/003 446/297 |
| 2007/0039624 A1 | 2/2007 | Roberts et al. | |
| 2008/0214089 A1 | 9/2008 | Vermac et al. | |
| 2009/0170056 A1 | 7/2009 | Nam et al. | |
| 2009/0315678 A1 * | 12/2009 | Padmanabhan | H04Q 9/00 340/10.1 |
| 2011/0181497 A1 | 7/2011 | Raviv | |
| 2012/0009845 A1 | 1/2012 | Schmelzer | |
| 2012/0136667 A1 * | 5/2012 | Emerick | G10L 15/22 704/275 |
| 2012/0197439 A1 * | 8/2012 | Wang | B25J 11/009 700/259 |
| 2012/0308973 A1 | 12/2012 | Marsac et al. | |
| 2013/0078600 A1 * | 3/2013 | Fischer | G09B 19/00 434/236 |
| 2014/0028712 A1 | 1/2014 | Keating et al. | |
| 2014/0113552 A1 | 4/2014 | Siddiqui | |
| 2014/0125678 A1 | 5/2014 | Wang et al. | |
| 2014/0222206 A1 * | 8/2014 | Mead | B25J 9/1697 700/259 |
| 2014/0314327 A1 | 10/2014 | Elliott | |
| 2015/0024837 A1 | 1/2015 | Ganz | |
| 2015/0050972 A1 | 2/2015 | Sarrafzadeh et al. | |
| 2015/0056588 A1 | 2/2015 | Bayer | |
| 2015/0133025 A1 | 5/2015 | Ponomarev et al. | |
| 2015/0328554 A1 | 11/2015 | Boeckle | |
| 2016/0019016 A1 | 1/2016 | Kochavi | |
| 2016/0027219 A1 | 1/2016 | Nuzzi | |
| 2016/0029962 A1 | 2/2016 | Hyde et al. | |
| 2016/0036898 A1 * | 2/2016 | Curtis | H04L 67/10 709/203 |
| 2016/0174901 A1 | 6/2016 | Majic | |

FOREIGN PATENT DOCUMENTS

| | | |
|---|---|---|
| WO | 2001069830 A3 | 6/2002 |
| WO | 2015192117 | 12/2015 |
| WO | 2017123175 A1 | 7/2017 |

OTHER PUBLICATIONS

Lenny the Lion, http://www.lenny-diabetes.com.
MySugr Junior, https://mysugr.com/apps/.
Scanimals, http://awesometoyblog.com/2013/02/25/toy-fair-2013-scanimals-combine-plush-toys-and-qr-codes/, Feb. 25, 2013.
Smart teddy bear knows how you feel, Tracy Staedter, Discovery News, Aug. 15, 2006.

* cited by examiner

SYSTEM, APPARATUS, AND METHOD FOR EDUCATING AND REDUCING STRESS FOR PATIENTS WITH ILLNESS OR TRAUMA USING AN INTERACTIVE LOCATION-AWARE TOY AND A DISTRIBUTED SENSOR NETWORK

RELATED APPLICATION DATA

This application claims the benefit of U.S. Provisional Patent Application No. 62/435,733, filed on Dec. 17, 2016, which is hereby incorporated by reference.

TECHNICAL FIELD

This application pertains to pediatric medicine, and more particularly, to a system, apparatus, and method for educating and reducing stress for patients with illness and trauma using an interactive location aware toy, and for tracking completion of care plans.

BACKGROUND

Visits to a doctor's office or hospital can be scary, especially for children. Children enter hospitals for a range of reasons, from acute conditions like a broken arm, to long-term treatment for chronic illnesses such as cancer. Regardless of the cause of entry, a hospital stay can be stressful for children and overwhelming for parents.

When a patient enters a hospital environment they are faced with a world of unknown devices, medical procedures, and people. For children, it is scary and stress inducing to have their blood drawn, go into a magnetic resonance imaging (MRI), or in the case of children with cancer, undergo chemotherapy. Doctors currently use distraction therapy techniques to help take the minds of children off of the medical procedures they are about to receive. A common example of this technique is using toys to distract children from the pain of their immunization injections.

For children, the location, context, and medium through which information is presented is paramount. While children may be given information by their doctor about a procedure before it occurs, this doesn't stop the fear that children experience when they actually step into the room where they will have an x-ray, have their blood drawn, or receive an MRI.

Children with chronic health conditions, such as childhood cancer, face repeated long-term hospital stays to receive treatment. For these children, simple distraction techniques don't necessarily ameliorate the fear, trauma, and emotional stress caused by repeated medical procedures. On top of the stress associated with the procedures themselves, children and their parents must abide by a care plan when in a hospital, going from appointment to appointment for the appropriate diagnostic procedures and treatments. It can be stressful for parents to manage their child's care plan and it can be overwhelming for children to be whisked from location to location within a hospital.

Providing rewards and incentives can help encourage children who face repeated medical procedures. Programs like BEADS OF COURAGE® exist for children with cancer, rewarding them for the completion of medical procedures with collectible beads. For kids, such programs can transform their procedures from a scary experience into a badge of honor. Reducing stress and providing education related to medical procedures can help improve feelings of self-efficacy, improve pediatric quality of life, and increase communication between parents and children. Further, interacting with the child through playtime exercises, for example with a doll, can spur information retention and stress reduction creating a fun and nurturing atmosphere.

Accordingly, a need remains for medical education, stress reduction, and care coordination that can be delivered through an inanimate object such as a doll and provided with the correct context, timing, and when the child is in the appropriate location. Providing education in this location-specific manner, through the friendly medium of a doll, can help calm children facing medical procedures and add an element of fun to otherwise scary experiences. Embodiments of the inventive concept address these and other limitations in the prior art.

Figure 1:
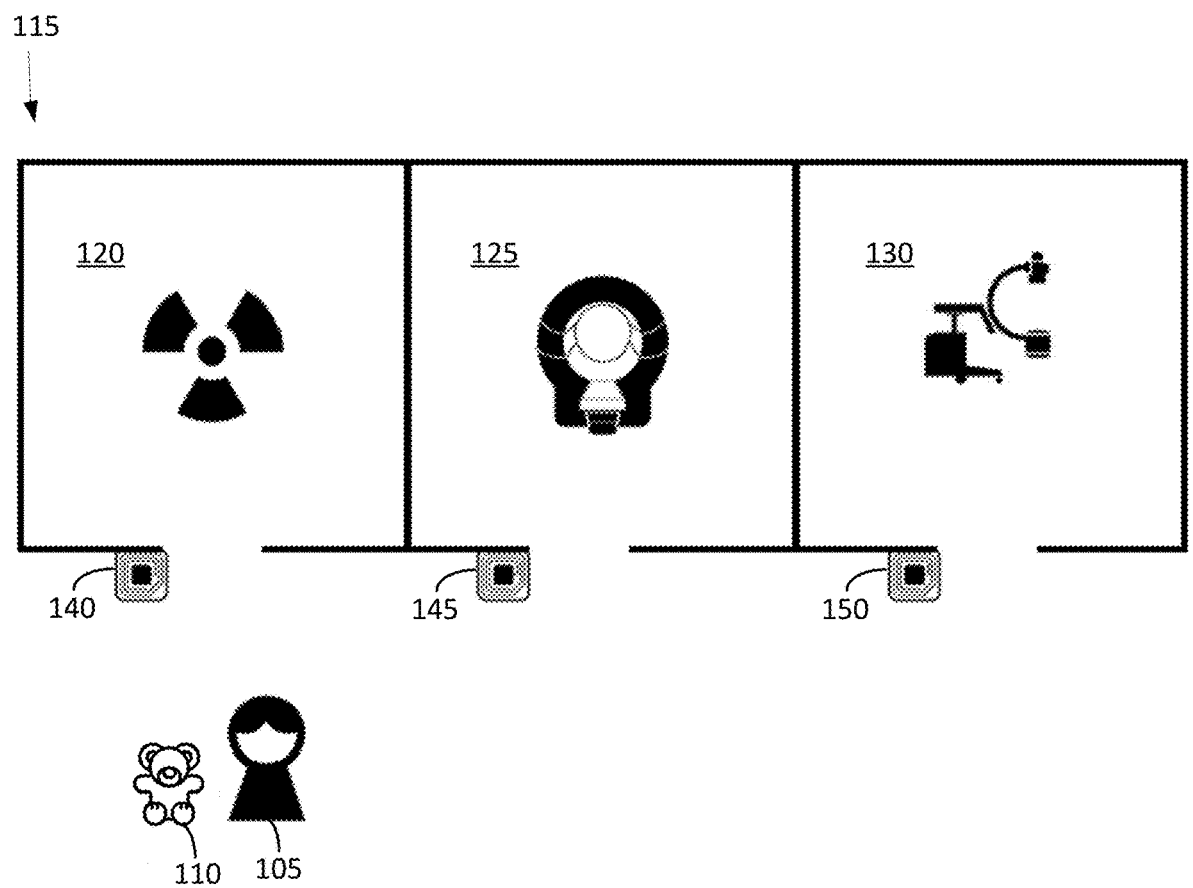
FIG. 1 is a top view showing three rooms of a healthcare facility such as hospital in accordance with some embodiments of the inventive concept.

The foregoing and other features of the inventive concept will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first sensor could be termed a second sensor, and, similarly, a second sensor could be termed a first sensor, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the present inventive concept include a smart toy and a method for educating patients about medical procedures and reducing stress associated with illness and trauma. The smart toy and method can be used as a tool to comfort children and provide entertainment during the treatment of health conditions. The smart toy and method can also be used to help patients follow a specific medical care plan given by their doctor. The smart toy described herein is aware of its location and thus provides patient education and stress relief in a way that is specific to the location of the patient within the healthcare facility and the treatments they are currently undergoing.

Embodiments include a system comprised of a smart toy, sensors placed in various rooms in a healthcare facility, a database that stores the location of the smart toy, and a computer or mobile interface that enables healthcare providers including doctors to input care plans for patients.

The term "smart toy" as used herein refers to an interactive doll that a child afflicted with a chronic illness or traumatic health condition may use to learn about and help manage that illness or condition. The smart toy may take the shape of a doll or animal and may be plush or hard. The smart toy may have a plurality of sensors connected via wires to an internal microprocessor or via wires or wirelessly to an external processor. The smart toy can include wireless connectivity through WIFI, a BLUETOOTH® connection to a mobile device, cellular and/or Global System for Mobile Communications (GSM) connection, or any other suitable form of wireless connectivity. The smart toy also can include an object identification system such that it can recognize sensors that are placed in various rooms of the healthcare facility. The object identification system may use near-filed communications (NFC), radio frequency identification (RFID), ZIGBEE®, a camera, and/or any other suitable form of object identification method.

Some embodiments of the smart toy may have accessories that resemble replicas of medical devices, enabling children to simulate medical procedures on the smart toy. Similar embodiments may also have accessories such as foods that enable children to care for and nurture the smart toy.

The system described herein can be implemented in a healthcare facility by placing sensors, or visually identifiable objects, in various rooms where care is performed. The patient is given a smart toy upon entry to the healthcare facility that is associated with the individual patient through a unique identifier (ID). As the patient moves between different rooms of the hospital, the smart toy's object identification system recognizes the sensors placed in the various rooms of the hospital. The identification of a sensor located in a hospital room triggers the smart toy to log its current location in an online database and provide a response to the patient that is correlated with the patient's current location. This location-aware response can be used to provide targeted education, emotional support, and entertainment to patients.

In some embodiments, doctors, nurses, and other healthcare professionals are provided with a software application that enables them to create care plans for patients. The term "care plan" as used herein refers to any combination of medical procedures, diagnostic tests, or appointments that are scheduled for a patient during their time in a healthcare facility. The software application communicates with the aforementioned online database to provide a status report that is updated in real time with the patient's location in the healthcare facility and their current progress through their care plan.

In other embodiments, the smart toy produces an audio or visual response to keep patients on track with their care plan. This can include reminders about the time of certain appointments or alerts to take medication.

Embodiments of the inventive concept may help children cope with a variety of health conditions including trauma, cancer, type 1 diabetes, sickle cell anemia, and/or congenital heart problems.

The following description and drawing figures describe aspects of a smart toy and method developed for use with children undergoing long hospital stays for cancer treatment. It will be understood that embodiments of the inventive concept can be adapted and used by children and adults experiencing any of the aforementioned health conditions and that the use of the invention is not limited to cancer treatments.

Figure 2:
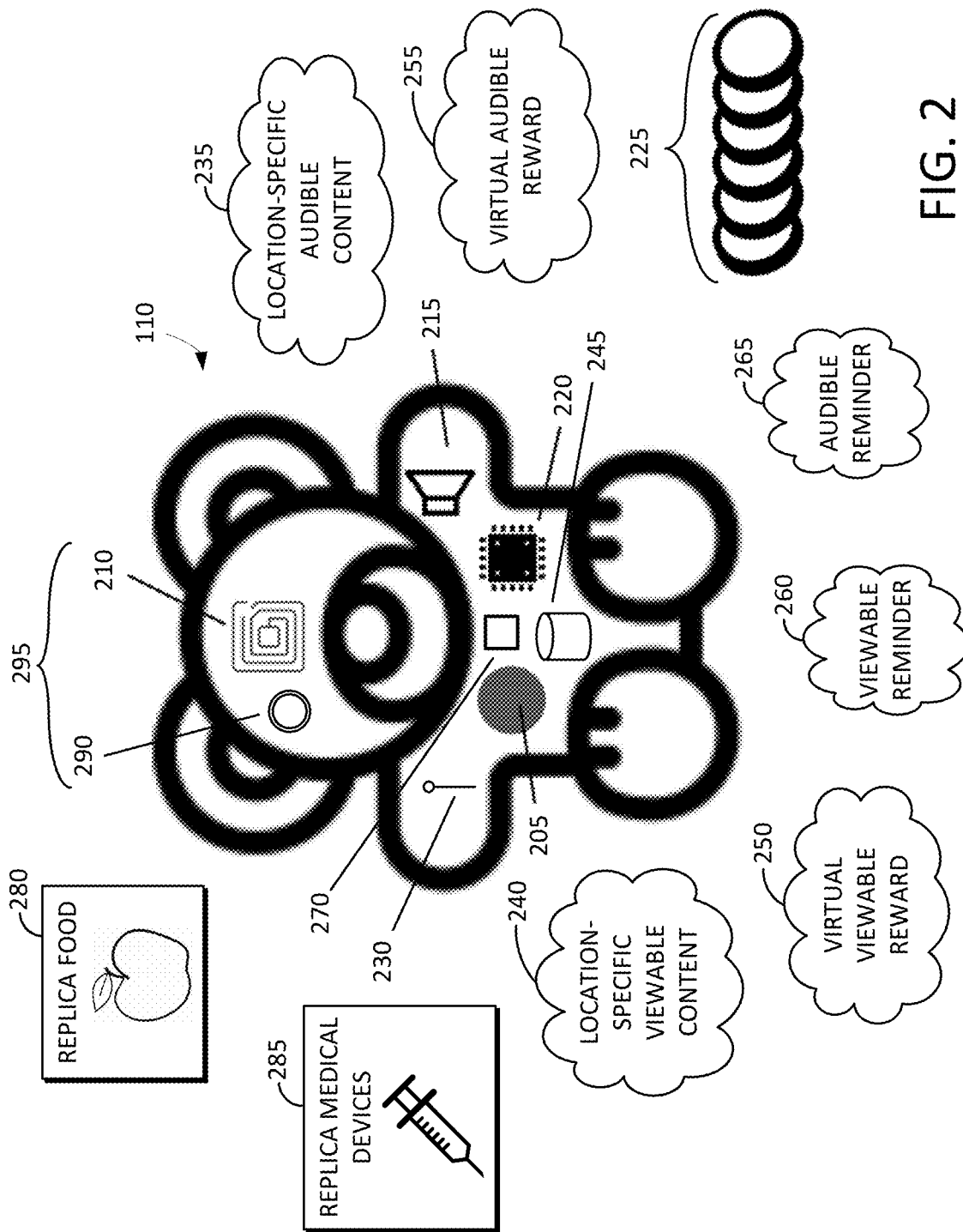
FIG. 2 is a schematic view of a toy in accordance with some embodiments of the inventive concept.
Figure 3:
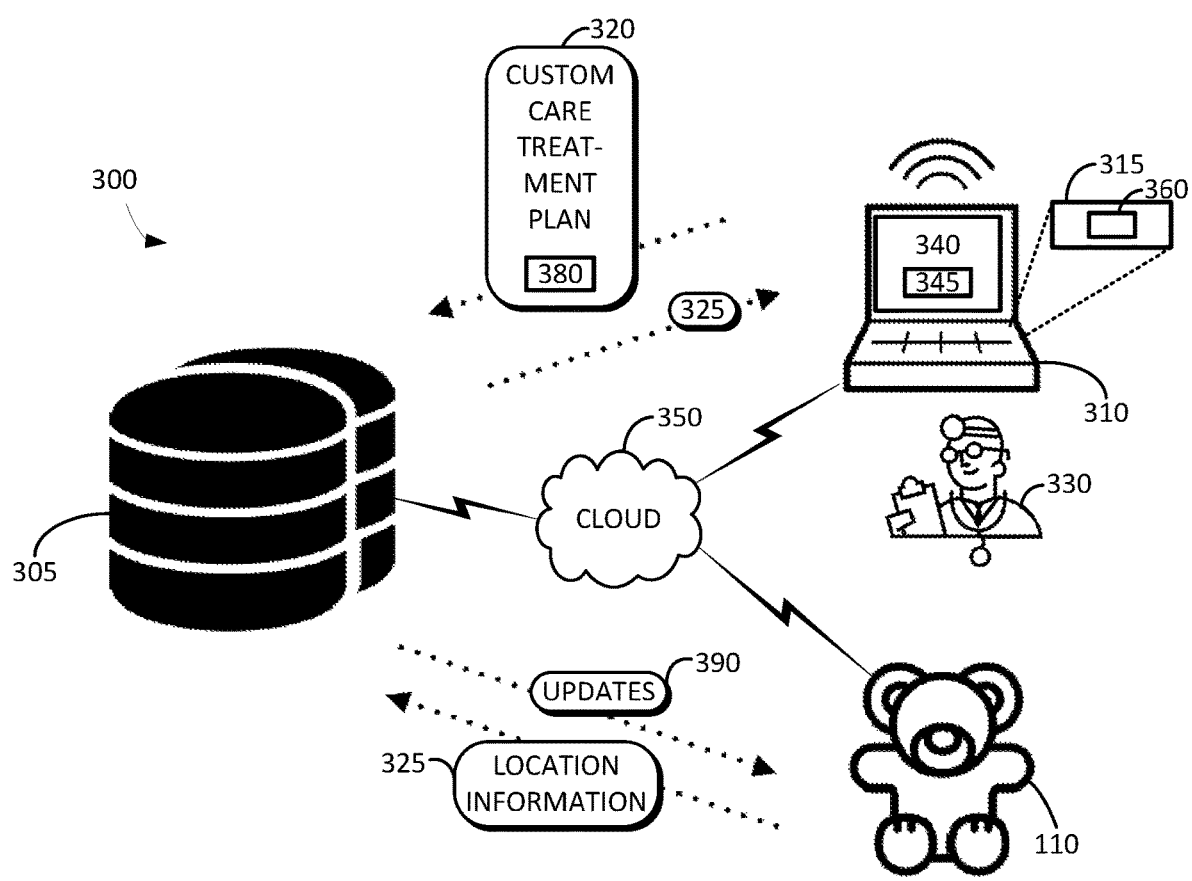
FIG. 3 is a schematic diagram of a portion of an interactive location-aware toy and distributed sensor network system in accordance with some embodiments of the inventive concept.

FIG. 1 is a top view showing three rooms of a healthcare facility 115 such as a hospital in accordance with some embodiments of the inventive concept. FIG. 2 is a schematic view of a smart toy 110 in accordance with some embodiments of the inventive concept. FIG. 3 is a schematic diagram of a portion of an interactive location-aware toy and distributed sensor network system 300 in accordance with some embodiments of the inventive concept. Reference is now made to FIGS. 1 through 3.

Referring to FIG. 2, the smart toy 110 may have a display screen 205, an object identifier 295, a wireless transceiver 230, a speaker 215, a camera 290, an internal storage device 245 such as a volatile or non-volatile memory, a reward tracking logic section 270, and a main computing unit 220. The main computing unit 220 can include a microprocessor, a central processing unit (CPU), an application specific integrated circuit (ASIC), a memory, a wireless communication logic, and/or a battery. Physical rewards such as tokens 225 can be "unlocked" or otherwise awarded to the child 105 based on the number of times the child 105 has visited certain locations, as further described below.

Referring to FIGS. 1 through 3, a child 105 is given a smart toy 110 when they enter a healthcare facility 115 such as a hospital to begin treatment for an illness such as cancer. It will be understood that while in this example the smart toy 110 is shown to be in the form of a bear, any suitable shape or kind of toy, such as a zebra, doll or other animal, can be used together with the other inventive aspects disclosed herein. Each room (e.g., 120, 125, and 130) of the healthcare facility 115 can be equipped with a corresponding location-identifying object (e.g., 140, 145, and 150) such that when the child 105 enters a particular room (e.g., room 120), the smart toy 110 can use its object identifier 295 to identify a particular specific location-identifying object (e.g., 140) associated with the particular room (e.g., 120), can store location information 325 in the internal storage device 245, and can transmit the location information 325 to an online database 305 using the wireless transceiver 230 via the cloud 350. The location identifying objects (e.g., 140, 145, and 150) can include a near-field communication (NFC) tag, an image that can be recognized by a camera such as a quick-response (QR) code, or other suitable unique object capable of identifying a location within the healthcare facility 115.

Upon activation of the object identifier 295 by a location-identifying object (e.g., 140, 145, or 150) in a room (e.g., 120, 125, or 130), the smart toy 110 can produce a response providing education and stress reduction content to the child 105 through a combination of the smart toy's display screen 205 and auditory cues from the smart toy's speaker 215. It will be understood that while the display screen 205 is shown in circular form, other shapes such as a rectangle or square can be used without departing from the inventive aspects disclosed herein.

In some embodiments, the object identifier 295 can read (e.g., sense or scan) and identify physical accessories that resemble replicas of medical devices 285, enabling children to simulate medical procedures on the smart toy 110. Similar embodiments may also have accessories such as replica foods 280 that are detected and identified using the object identifier 295, which enable children to care for and nurture the smart toy 110.

A healthcare provider 330 such as a doctor, nurse, or other healthcare professional can use a computer terminal 310 that includes a medical education and stress reduction logic section 315, which can include a custom care plan logic section 360 to create a custom care treatment plan 320 for the child 105 in accordance with the necessary treatment for their illness. The custom care treatment plan 320 can be synchronized with the online database 305 via the cloud 350, and associated with the smart toy 110, through a unique identifier (ID) 380. In other words, the online database 305 can store multiple custom care treatment plans (e.g., 320) each having a unique ID (e.g., 380) associated therewith. The custom care treatment plan 320 can include a custom medication adherence plan as further described below. It will be understood that the computer terminal 310 can include a desktop computer terminal, a laptop or notebook computer terminal, a tablet computer terminal, a smart phone, or other suitable mobile or fixed computer device.

As the child 105 travels to different locations of the healthcare facility 115 for treatments, such as radiation therapy in room 120, an MRI in room 125, or an X-ray in room 130, the smart toy 110 logs their location information 325 in the online database 305 via the cloud 350, and the location information 325 can be made viewable to the healthcare provider 330 such as a doctor through the computer terminal 310. The healthcare provider 330 can view the location information (e.g., 325) for each of many different children (e.g., 105) that come to the healthcare facility 115. In other words, the healthcare provider 330 can view in the aggregate the location information 325. Accordingly, the healthcare provider 330 can determine or otherwise assess operational efficiency of the healthcare facility 115.

Upon entry to different treatment locations (e.g., rooms 120, 125, or 130), the smart toy 110 can provide location-specific audible content 235 and/or location-specific viewable content 240 to the child 105 that is specific to the location information 325 and the child 105. For example, when the child 105 enters the radiation therapy room 120, the smart toy 110 can explain, using the speaker 215, the purpose of radiation in eliminating cancer cells and then tell the child 105 a story about a time that the smart toy 110 received radiation therapy and how it made them feel. By way of another example, the smart toy 110 can display, using the display screen 205, information about radiation therapy.

Upon repeated visits to the radiation therapy room 120, the smart toy's response and provided content can be different and may encourage the child 105 by congratulating them on the number of times they've already completed radiation therapy. In other words, the smart toy 110 can keep track of a number of times that the child 105 has visited each room in the healthcare facility 115, and modify the location-specific audible content 235 and/or the location-specific viewable content 240 depending on the number of visits to each room. In some embodiments, the smart toy 110 can remind the child 105 when to attend appointments or take a medication through auditory reminders 265 given from the smart toy's speaker 215. Alternatively or in addition, the smart toy 110 can remind the child 105 when to attend appointments or take a medication by way of a viewable reminder 260 displayed on the smart toy's display screen 205. The internal storage device 245 can store the location-specific audible content 235, the location-specific viewable content 240, and the reminders (e.g., 260 and/or 265).

By way of another example, the healthcare provider 330 may take blood samples from the child 105 to determine whether chemotherapy is needed. While the blood samples are being tested, the smart toy 110 can console the child 105. Prior to attaching a chemotherapy delivery port to the child 105, information about what is about to happen can be provided to the child 105 through the smart toy 110. The chemotherapy information can be location-specific to the particular room within the healthcare facility 115. If the blood work performed indicates that no chemotherapy is needed for that visit, the smart toy 110 can inform the child 105 that a chemotherapy treatment has been postponed. Otherwise, the smart toy 110 can help prepare the child 105 for the chemotherapy.

In some embodiments, the healthcare provider 330 such as a doctor can use the computer terminal 310 including the medical education and stress reduction logic section 315, which can include the custom care plan logic section 360 to create custom medication adherence plans (e.g., 320) for children, which can be stored in the online database 305 via the cloud 350. When it is time for the child 105 to take a medication, a reminder (e.g., 260 and/or 265) can be provided through the smart toy 110, via the smart toy's display screen 205 and/or via auditory cues from the smart toy's speaker 215.

In some embodiments, the smart toy 110 automatically receives and installs functionality and/or content updates 390 from the online database 305 via the cloud 350 to deploy new features and functionality as the child 105 completes repeated visits to certain care locations in the healthcare facility 115 such as rooms 120, 125, and/or 130. The internal storage device 245 can receive and store the functionality and/or content updates 390.

Child life specialists, nurses, or other healthcare professionals can also access the computer terminal 310, to monitor progress of the child 105 through their custom care treatment plan 320. Based on the number of times they've visited certain locations (e.g., 120, 125, or 130) as stored in the online database 305, physical rewards can be unlocked such as the physical tokens 225. It will be understood that the rewards can include other physical items such as stickers, beads, or additional toys. The smart toy 110 can inform the child 105 that a physical reward 225 has been unlocked via the display screen 205 and/or the speaker 215. The child 105 can then collect the physical reward 225 from the healthcare provider 330. The reward tracking logic section 270 may keep track of the number of times the child 105 has visited different locations (e.g., 120, 125, or 130) of the healthcare facility 115 and unlock the rewards when a predefined threshold number of visits for a particular location has been met. The reward tracking logic section 270 may cause the display screen 205 and/or the speaker 215 to inform the child 105 about the unlocked rewards, which may then be collected. Alternatively or in addition, the reward tracking logic section 270 may be operable within the computer terminal 310 as further explained below.

Accordingly, the smart toy 110 can provide calming effects and can educate the child 105 in a healthcare facility 115 such as a hospital. The child 105 can be provided with the smart toy 110 upon beginning their experience or journey at the healthcare facility 115. The smart toy 110 can include an object identification system having the object identifier 295, wireless connectivity using the wireless transceiver 230, the speaker 215, the display screen 205, and the internal storage device 245. The internal storage device 245 can store the educational content and strategies (e.g., 235 and 240) to help the child 105 and the parents or guardians of the child 105 manage stress. The wireless transceiver 230 of the smart toy 110 can establish a connection to the online database 305 via the cloud 350, and may periodically receive additional educational content and stress management strategies.

The smart toy 110 can use its object identification system including the object identifier 295 upon entry to a room (e.g., 120, 125, and 130) in the healthcare facility 115 to read a corresponding location-identifying object (e.g., 140, 145, and 150) located in or nearby the room, which can assist the smart toy 110 in identifying its current location. The term "read" herein can mean either sense or scan, or both. For example, in some embodiments, the object identifier 295 is an NFC sensor 210, which can sense an NFC tag. By way of another example, in some embodiments, the object identifier 295 is a camera 290, which can sense an image such as a QR code. The smart toy 110 can include either the NFC sensor 210 for sensing or the camera 290 for scanning, or both. A location-specific response of the smart toy 110 can be triggered from the internal storage device 245, or queried from the online database 305 via the cloud 350. The location of the smart toy 110, and thus the child 105 by inference, can be stored in the internal storage device 245 and/or the online database 305 to be used for tracking the child 105, for unlocking physical or virtual rewards, for unlocking physical or virtual incentives, and to improve the intelligence of the smart toy 110. The response and strategies employed by the smart toy 110 can be enhanced over time based on the information gathered and stored in the internal storage device 245 and/or in the online database 305. By way of another example, the object identifier 295 may scan an anatomical map of a body that is located in a room of the healthcare facility 115, and then the smart toy 110 can provide information specific to the scanned anatomical map to the child 105 via the display screen and/or the speaker 215. By way of yet another example, an X-ray image may be scanned by the object identifier 295 and information about the X-ray image may be provided to the child 105 via the display screen and/or the speaker 215.

New functionalities of the smart toy 110 can be revealed to the child 105 upon repeated location entries in the online database 305. The child 105 can receive physical rewards 225 in the forms of tokens, stickers, toys, or similar items when repeated check-ins occur at specific locations. Alternatively or in addition, the child 105 can receive virtual rewards (e.g., 250 and 255) in the forms of virtual tokens, stickers, toys, games, or similar items displayed via the display 205 or sounded through the speaker 215 when repeated check-ins occur at specific locations. For example, virtual rewards can include a virtual viewable reward 250 shown on the display screen 205 and/or a virtual audible reward 255 emitted by the speaker 215.

In some embodiments, the location-identifying objects (e.g., 140, 145, and 150) located in or nearby the rooms (e.g., 120, 125, and 130) are passive near-field communication (NFC) tags. In some embodiments, the location-identifying objects (e.g., 140, 145, and 150) located in or nearby the rooms (e.g., 120, 125, and 130) are images such as QR codes. In some embodiments, the location-identifying objects (e.g., 140, 145, and 150) located in or nearby the rooms (e.g., 120, 125, and 130) are some other unique object, which can identify a location. In the case where the location-identifying objects (e.g., 140, 145, and 150) are NFC tags, the child 105 can hold the smart toy 110 within a certain proximity of a particular passive NFC tag so that the smart toy 110 can read the NFC tag using the smart toy's NFC sensor 210, for example, and register its location in the internal storage device 245 and/or with the online database 305. In the case where the location-identifying objects (e.g., 140, 145, and 150) are images, the child 105 can hold the smart toy 110 within a certain proximity of a particular image (e.g., 140) so that the smart toy 110 can scan the image using the smart toy's camera 290, for example, and register its location in the internal storage device 245 and/or with the online database 305. In other words, the image can uniquely represent a particular location in the healthcare facility 115. And the act of scanning the image confirms the presence of the smart toy 110, and by inference the child 105, at that location. In the case where the location-identifying objects (e.g., 140, 145, and 150) are some other unique objects, the child 105 can hold the smart toy 110 within a certain proximity of a particular unique object (e.g., 140) so that the smart toy 110 can scan the unique object using the smart toy's camera 290, for example, and register its location in the internal storage device 245 and/or with the online database 305.

The healthcare provider 330 can provide a custom care treatment plan 320 to the child 105 via the smart toy 110. Progress through the custom care treatment plan 320 can be tracked over time. The healthcare provider 330 can use the computer terminal 310 to set up the custom care treatment plan 320 for the child 105 comprising any number of tests or treatments. The custom care treatment plan 320 can be stored in the online database 305 where it is associated with the unique patient ID 380.

The child 105 can be given the smart toy 110 that is associated with their unique patient ID 380. The smart toy 110 can include the object identifier 295. In some embodiments, the object identifier 295 is an NFC sensor 210, which can read one or more NFC tags. In some embodiments, the object identifier 295 is a camera 290, which can scan one or more images or other unique objects. The smart toy 110 can store, in the internal storage device 245 and/or the online database 305, educational content and strategies to help the child 105 and their parents manage stress. The smart toy 110 can establish a wireless connection to the online database 305 via the cloud 350, and can receive additional educational content and stress management strategies (e.g., updates 390) periodically from the online database 305 via the cloud 350.

The smart toy 110 can use its object identification system including the object identifier 295 upon entry to a room (e.g., 120, 125, or 130) in a healthcare facility 115 to read a location-identifying object (e.g., 140, 145, and 150) located in or nearby the room, and can therefore identify its current location. The location information 325 can be logged in the online database 350. The location information 325 can be used to track the progress of the child 105 through their custom care treatment plan 320.

The display screen 205 of the smart toy 110 can show the child 105 specific steps to follow in their custom care treatment plan 320. The speaker 215 of the smart toy 110 can audibly read out to the child 105 the custom care treatment plan 320. The healthcare provider 330 can be provided with a graphical user interface dashboard 340, which shows the real time location information 325 of the child 105, and progress through their custom care treatment plan 320. The smart toy 110 can give an audible reminder 265 and/or a viewable reminder 260 of where child 105 should go for the next phase or set of steps in their custom care treatment plan 320. These reminders (e.g., 260 and/or 265) can be triggered based on appointment times 345 set in the graphical user interface dashboard 340 via the computer terminal 310 by the healthcare provider 330.

Figure 4:
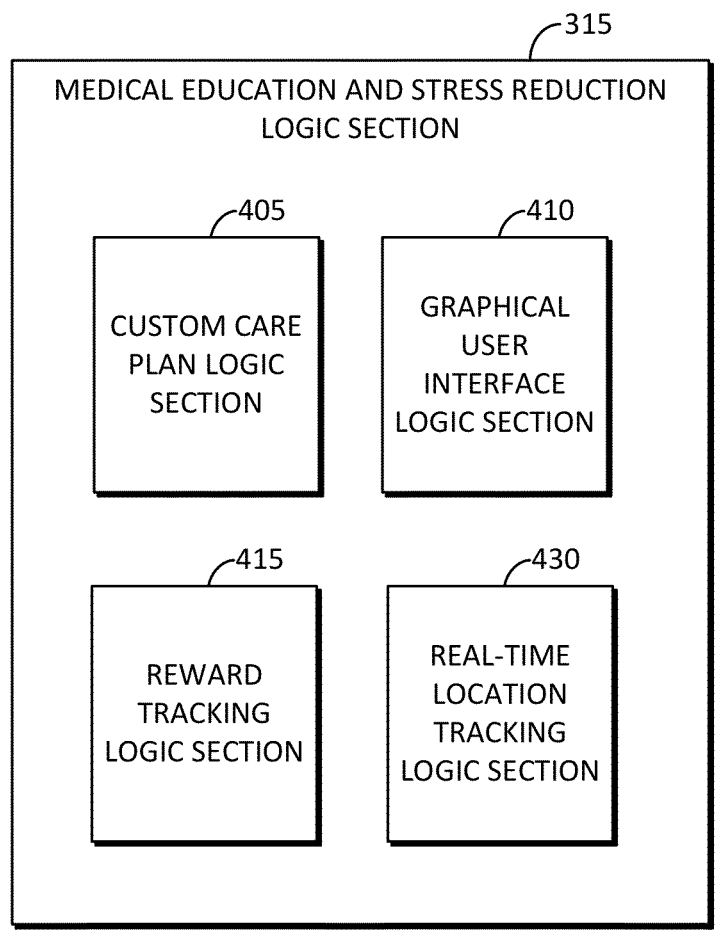
FIG. 4 illustrates a block diagram of a medical education and stress reduction logic section in accordance with some embodiments of the inventive concept.
Figure 5:
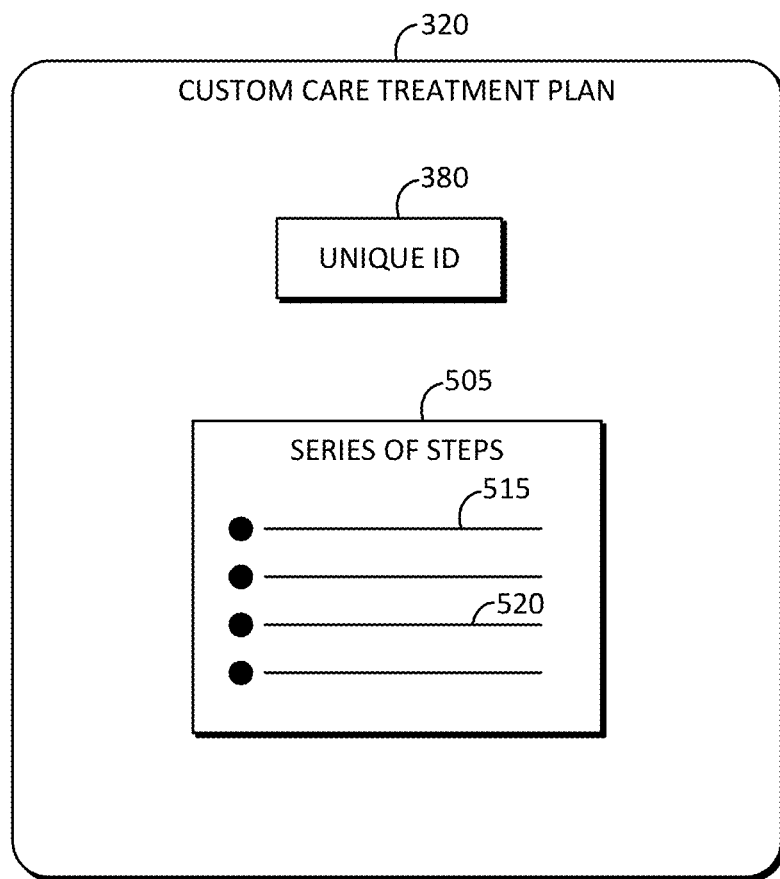
FIG. 5 illustrates a block diagram of a custom care treatment plan in accordance with some embodiments of the inventive concept.

FIG. 4 illustrates a block diagram of the medical education and stress reduction logic section 315 in accordance with some embodiments of the inventive concept. FIG. 5 illustrates a block diagram of a custom care treatment plan 320 in accordance with some embodiments of the inventive concept. Reference is now made to FIGS. 1 through 5.

The medical education and stress reduction logic section 315 can include a custom care plan logic section 405, a graphical user interface logic section 410, a reward tracking logic section 415, and a real-time location tracking logic section 430.

A system 300 for educating and reducing stress for patients with illness or trauma is disclosed herein. More specifically, the system 300 can include multiple location-identifying objects (e.g., 140, 145, and 150) each disposed proximally to a corresponding room (e.g., 120, 125, and 130) among a plurality of rooms of a healthcare facility 115. The system 300 can include an online database 305 communicatively coupled to the cloud 350. The system 300 can include a smart toy 110 including an object identifier 295 that is configured to sense or scan a particular location-identifying object (e.g., 140) from among the plurality of location-identifying objects (e.g., 140, 145, and 150). The smart toy 110 can include a wireless transceiver 230 configured to transmit location information 325 about the smart toy 110 to the online database 305 via the cloud 350. The location information 325 is dependent on the sensed particular location-identifying object (e.g., 140) from among the plurality of location-identifying objects (e.g., 140, 145, and 150).

The system 300 can include an education and stress reduction logic section 315 operable with a computer terminal 310. The education and stress reduction logic section 315 can be communicatively coupled to the online database 305 via the cloud 350. The education and stress reduction logic section 315 can include a graphical user interface logic section 410 that is configured to present a graphical user interface 340 via a display screen of the computer terminal 310. The education and stress reduction logic section 315 can include a real-time location tracking logic section 430 that is configured to receive the location information 325 from the online database 305, and to track a real-time location of the smart toy 110 within the healthcare facility 115 based on the received location information 325. The graphical user interface 340 can be configured to display the real-time location of the smart toy 110 within the healthcare facility 115.

In some embodiments, the smart toy 110 includes a display screen 205, a speaker 215, and a reward tracking logic section 270. The reward tracking logic section 270 can be configured to track a number of times the object identifier 295 of the smart toy 110 senses or scans the particular location-identifying object (e.g., 140) from among the plurality of location-identifying objects (e.g., 140, 145, and 150). The reward tracking logic section 270 can be configured to cause the display screen 205 and/or the speaker 215 of the smart toy 110 to inform the child 105 about an unlocked reward (e.g., 225, 250, and/or 255) responsive to the number of times exceeding a predefined threshold number of times that triggers the reward.

In some embodiments, the education and stress reduction logic section 315 includes a reward tracking logic section 415. In this embodiment, the reward tracking logic section 415 can be configured to track the number of times the object identifier 295 of the smart toy 110 senses or scans the particular location-identifying object (e.g., 140) from among the plurality of location-identifying objects (e.g., 140, 145, and 150). The reward tracking logic section 415 can be configured to cause the display screen 205 and/or the speaker 215 of the smart toy 110 to inform the child 105 about an unlocked reward (e.g., 225, 250, and/or 255) responsive to the number of times exceeding a predefined threshold number of times that triggers the reward.

In some embodiments, the custom care plan logic section 405 is configured to create a custom care treatment plan 320 for the child 105. The custom care treatment plan 320 can be dependent on input received via the graphical user interface 340 from the healthcare provider 330. The custom care treatment plan 320 can be dependent on the location information 325 that represents the journey of the child 105 through the healthcare facility 115. The custom care treatment plan 320 can include a series of steps 505 for the child 105 to follow. The display screen 205 of the smart toy 110 can be configured to show the series of steps 505 for the child 105 to follow to complete the custom care treatment plan 320.

In some embodiments, the custom care plan logic section 405 is configured to track progress of the child 105 in completing the series of steps 505 of the custom care treatment plan 320. The graphical user interface 340 can be configured to display the tracked progress of the child 105 in completing the series of steps 505 of the custom care treatment plan 320. The series of steps 505 of the custom care treatment plan can include at least one medical test 515 and at least one medical treatment 520. The custom care treatment plan 320 can include a unique identifier 380 associated with the smart toy 105 and/or associated with the child 105. The online database 305 can be configured to receive and store the custom care treatment plan 320 including the unique identifier 380. The smart toy 110 can be configured to access, using the wireless transceiver 230 of the smart toy 110 via the cloud 350, the custom care treatment plan 320 stored in the online database 305.

In some embodiments, the smart toy 110 includes a speaker 215, an internal storage device 245, and a microprocessor 220. The internal storage device 245 can be configured to store location-specific viewable content 240, one or more viewable reminders 260, location-specific audible content 235, and/or one or more audible reminders 265. The microprocessor 220 can be configured to cause the location-specific viewable content 240 to be displayed on the display screen 205 of the smart toy 110 responsive to the object identifier 295 sensing or scanning the particular location-identifying object (e.g., 140) from among the plurality of location-identifying objects (e.g., 140, 145, and 150).

The microprocessor 220 can be configured to cause the location-specific audible content 235 to be emitted via the speaker 215 of the smart toy 110 responsive to the object identifier 295 sensing or scanning the particular location-identifying object (e.g., 140) from among the plurality of location-identifying objects (e.g., 140, 145, and 150).

The microprocessor 220 can be configured to cause the one or more viewable reminders 260 to be displayed on the display screen 205 of the smart toy 110. Alternatively or in addition, the microprocessor 220 can be configured to cause the one or more audible reminders 265 to be emitted via the speaker 215 of the smart toy 110. The one or more viewable reminders 260 can include a reminder about a medical appointment or a reminder about when to take a medication, for example. Similarly, the one or more audible reminders 265 can include a reminder about a medical appointment or a reminder about when to take a medication, for example.

The wireless transceiver 230 of the smart toy 110 can be configured to periodically receive one or more functionality updates 390 from the online database 305. This can happen automatically or in response to a manual update request received by the smart toy 110. The internal storage device 245 of the smart toy 110 can be configured to store the one or more functionality updates 390.

In some embodiments, the system 300 for educating and reducing stress for patients with illness or trauma can include a smart toy 110 having an object identifier 295, an internal storage device 245, and a microprocessor 220. In some embodiments, the object identifier 295 is configured to read a particular location-identifying object (e.g., 140) from among the plurality of location-identifying objects (e.g., 140, 145, and 150). The internal storage device 245 can store location-specific content (e.g., 240 and 235). In some embodiments, the microprocessor 220 is configured to cause the location-specific content (e.g., 240 and 235) to be provided to the child 105 via the smart toy 110 responsive to the object identifier 295 reading the particular location-identifying object (e.g., 140) from among the plurality of location-identifying objects (e.g., 140, 145, and 150). The particular location-identifying object (e.g., 140) may be referred to as a first particular location-identifying object. The location-specific content (e.g., 240 and 235) may be referred to as first location-specific content. The object identifier 295 is configured to read a second particular location-identifying object (e.g., 145) from among the plurality of location-identifying objects (e.g., 140, 145, and 150). In some embodiments, the internal storage device 245 is configured to store second location-specific content (e.g., 240 or 235). In other words, the internal storage device 245 can store various location-specific content associated with the various different rooms (e.g., 120, 125, and 130) of the healthcare facility 115. The microprocessor 220 can cause the second location-specific content (e.g., 240 or 235) to be provided to the child 105 via the smart toy 110 responsive to the object identifier 295 reading the second particular location-identifying object (e.g., 145) from among the plurality of location-identifying objects (e.g., 140, 145, and 150). In some embodiments, the location-specific viewable content 240 includes at least one of an image related to a childhood illness, an instruction related to childhood illness, or information about a medical procedure. In some embodiments, the location-specific audible content 235 includes at least one of an image related to a childhood illness, an instruction related to childhood illness, or information about a medical procedure.

A method for educating and reducing stress for patients with illness or trauma is also disclosed herein. More specifically, the method can include disposing multiple near location-identifying object (e.g., 140, 145, and 150) proximally to a corresponding room (e.g., 120, 125, and 130) among a plurality of rooms of a healthcare facility 115. The method can include causing an object identifier 295 to sense or scan a particular location-identifying object (e.g., 140) from among the plurality of location-identifying object (e.g., 140, 145, and 150). The method can include transmitting, by a wireless transceiver 230 of a smart toy 110, location information 325 about the smart toy 110 to the online database 305 via the cloud 350. The location information 325 can be dependent on the sensed particular location-identifying object (e.g., 140) from among the plurality of location-identifying objects (e.g., 140, 145, and 150).

The method can include educating and reducing stress of the child 105 and the child's parents, using an education and stress reduction logic section 315 that is operable with a computer terminal 310. The method can include communicatively coupling the education and stress reduction logic section 315 to the online database 305 via the cloud 350. The method can include presenting, by a graphical user interface logic section 410 of the education and stress reduction logic section 315, a graphical user interface 340 via a display screen of the computer terminal 310. The method can include receiving, by a real-time location tracking logic section 430 of the education and stress reduction logic section 315, the location information 325 from the online database 305, and tracking a real-time location of the smart toy 110 within the healthcare facility 115 based on the received location information 325. The method can include displaying, by the graphical user interface 340, the real-time location of the smart toy 110 within the healthcare facility 115.

In some embodiments, the method can include tracking, by the reward tracking logic section 270, a number of times the object identifier 295 of the smart toy 110 senses or scans the particular location-identifying object (e.g., 140) from among the plurality of location-identifying objects (e.g., 140, 145, and 150). The method can include causing, by the reward tracking logic section 270, the display screen 205 and/or the speaker 215 of the smart toy 110 to inform the child 105 about an unlocked reward (e.g., 225, 250, and/or 255) responsive to the number of times exceeding a predefined threshold number of times that triggers the reward.

In some embodiments, the method can include tracking, by the reward tracking logic section 415, the number of times the object identifier 295 of the smart toy 110 senses or scans the particular location-identifying object (e.g., 140) from among the plurality of location-identifying objects (e.g., 140, 145, and 150). The method can include causing, by the reward tracking logic section 415, the display screen 205 and/or the speaker 215 of the smart toy 110 to inform the child 105 about an unlocked reward (e.g., 225, 250, and/or 255) responsive to the number of times exceeding a predefined threshold number of times that triggers the reward.

In some embodiments, the method can include creating, by the custom care plan logic section 405, a custom care treatment plan 320 for the child 105. The custom care treatment plan 320 can be dependent on input received via the graphical user interface 340 from the healthcare provider 330. The method can include creating a series of steps 505 for the child 105 to follow. The method can including showing on the display screen 205 of the smart toy 110 the series of steps 505 for the child 105 to follow to complete the custom care treatment plan 320.

In some embodiments, the method can include tracking progress of the child 105, by the custom care plan logic section 405, in completing the series of steps 505 of the custom care treatment plan 320. The method can include displaying, by the graphical user interface 340, the tracked progress of the child 105 in completing the series of steps 505 of the custom care treatment plan 320. The series of steps 505 of the custom care treatment plan can include at least one medical test 515 and at least one medical treatment 520. The method can include associating a unique identifier 380 with the smart toy 105 and/or with the child 105. The method can include receiving and storing, by the online database 305, the custom care treatment plan 320 including the unique identifier 380. The method can include accessing, by the smart toy 110, using the wireless transceiver 230 of the smart toy 110 via the cloud 350, the custom care treatment plan 320 stored in the online database 305.

The method can include storing, by the internal storage device 245, location-specific viewable content 240, one or more viewable reminders 260, location-specific audible content 235, and/or one or more audible reminders 265. The method can include causing, by the microprocessor 220, the location-specific viewable content 240 to be displayed on the display screen 205 of the smart toy 110 responsive to the object identifier 295 sensing or scanning the particular location-identifying object (e.g., 140) from among the plurality of location-identifying objects (e.g., 140, 145, and 150).

The method can include causing, by the microprocessor 220, the location-specific audible content 235 to be emitted via the speaker 215 of the smart toy 110 responsive to the object identifier 295 sensing or scanning the particular location-identifying object (e.g., 140) from among the plurality of location-identifying objects (e.g., 140, 145, and 150).

The method can include causing, by the microprocessor 220, the one or more viewable reminders 260 to be displayed on the display screen 205 of the smart toy 110. Alternatively or in addition, the method can include causing, by the microprocessor 220, the one or more audible reminders 265 to be emitted via the speaker 215 of the smart toy 110. The one or more viewable reminders 260 can include a reminder about a medical appointment or a reminder about when to take a medication, for example. Similarly, the one or more audible reminders 265 can include a reminder about a medical appointment or a reminder about when to take a medication, for example.

The method can include periodically receiving, by the wireless transceiver 230 of the smart toy 110, one or more functionality updates 390 from the online database 305. This can happen automatically or in response to a manual update request received by the smart toy 110. The method can include storing, by the internal storage device 245 of the smart toy 110, the one or more functionality updates 390.

Embodiments are described herein, and illustrated in the drawings, in terms of functional blocks, units and/or modules. Those skilled in the art will appreciate that these blocks, units and/or modules can be physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

The following discussion is intended to provide a brief, general description of a suitable machine or machines in which certain aspects of the inventive concept can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the inventive concept can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the inventive concept with reference to illustrated embodiments, it will be recognized that the illustrated embodiments can be modified in arrangement and detail without departing from such principles, and can be combined in any desired manner And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the inventive concept to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the embodiments as described herein.

Consequently, in view of the wide variety of permutations to the embodiments described herein, this detailed description and accompanying material is intended to be illustrative only, and should not be taken as limiting the scope of the inventive concept. What is claimed as the invention, therefore, is all such modifications as may come within the scope and spirit of the following claims and equivalents thereto.

The invention claimed is:

1. A system for educating and reducing stress for patients with illness or trauma, comprising:
   a plurality of location-identifying objects each disposed proximally to a corresponding room among a plurality of rooms of a healthcare facility;
   an online database communicatively coupled to a cloud;
   a smart toy including an object identifier configured to read a particular location-identifying object from among the plurality of location-identifying objects, and including a wireless transceiver configured to transmit location information about the smart toy to the online database via the cloud, wherein the location information is dependent on the read particular location-identifying object from among the plurality of location-identifying objects; and
   an education and stress reduction logic section operable with a computer terminal, wherein the education and stress reduction logic section is communicatively coupled to the online database via the cloud;
   wherein:
   the smart toy further includes a speaker, an internal storage device, and a microprocessor;
   the internal storage device is configured to store location-specific viewable content, one or more viewable reminders, location-specific audible content, and one or more audible reminders;
   the microprocessor is configured to cause the location-specific viewable content to be displayed on a display screen of the smart toy responsive to the object identifier reading the particular location-identifying object from among the plurality of location-identifying objects;
   the microprocessor is configured to cause the location-specific audible content to be emitted via the speaker of the smart toy responsive to the object identifier reading the particular location-identifying object from among the plurality of location-identifying objects;
   the microprocessor is configured to cause the one or more viewable reminders to be displayed on the display screen of the smart toy;
   the microprocessor is configured to cause the one or more audible reminders to be emitted via the speaker of the smart toy;
   the one or more viewable reminders includes at least one of a reminder about a medical appointment or a reminder about when to take a medication; and
   the one or more audible reminders includes at least one of a reminder about the medical appointment or a reminder about when to take the medication.

2. The system of claim 1, wherein the education and stress reduction logic section includes:
   a graphical user interface logic section configured to present a graphical user interface via the display screen of the computer terminal; and
   a real-time location tracking logic section configured to receive the location information from the online database, and to track a real-time location of the smart toy within the healthcare facility based on the received location information, wherein the graphical user interface is configured to display the real-time location of the smart toy within the healthcare facility.

3. The system of claim 2, wherein:
   the smart toy includes a reward tracking logic section;
   the reward tracking logic section is configured to track a number of times the object identifier of the smart toy reads the particular location-identifying object from among the plurality of location-identifying objects; and
   the reward tracking logic section is configured to cause at least one of the display screen or the speaker of the smart toy to inform a child about an unlocked reward responsive to the number of times exceeding a predefined threshold.

4. The system of claim 2, wherein:
   the education and stress reduction logic section includes a reward tracking logic section;
   the reward tracking logic section is configured to track a number of times the object identifier of the smart toy reads the particular location-identifying object from among the plurality of location-identifying objects; and
   the reward tracking logic section is configured to cause at least one of the display screen or the speaker of the smart toy to inform a child about an unlocked reward responsive to the number of times exceeding a predefined threshold.

5. The system of claim 1, wherein the education and stress reduction logic section includes:
   a graphical user interface logic section configured to present a graphical user interface via the display screen of the computer terminal; and
   a custom care plan logic section configured to create a custom care treatment plan for a child, wherein the custom care treatment plan is dependent on input received via the graphical user interface from a healthcare provider.

6. The system of claim 5, wherein:
   the custom care treatment plan includes a series of steps for the child to follow; and the display screen is configured to show the series of steps for the child to follow to complete the custom care treatment plan.

7. The system of claim 6, wherein:
the custom care plan logic section is configured to track progress of the child in completing the series of steps of the custom care treatment plan; and
the graphical user interface is configured to display the tracked progress of the child in completing the series of steps of the custom care treatment plan.

8. The system of claim 6, wherein the series of steps of the custom care treatment plan includes at least one medical test and at least one medical treatment.

9. The system of claim 6, wherein:
the custom care treatment plan includes a unique identifier associated with the smart toy; and
the online database is configured to receive and store the custom care treatment plan including the unique identifier.

10. The system of claim 6, wherein the smart toy is configured to access, using the wireless transceiver of the smart toy via the cloud, the custom care treatment plan stored in the online database.

11. The system of claim 1, wherein:
the wireless transceiver of the smart toy is configured to periodically receive one or more functionality updates from the online database; and
the internal storage device of the smart toy is configured to store the one or more functionality updates.

12. The system of claim 1, wherein the object identifier of the smart toy is configured to read and identify one or more replica food items.

13. The system of claim 1, wherein the object identifier of the smart toy is configured to read and identify one or more replica medical devices.

14. A system for educating and reducing stress for patients with illness or trauma, comprising:
a plurality of location-identifying objects each disposed proximally to a corresponding room among a plurality of rooms of a healthcare facility; and
a smart toy including an object identifier, an internal storage device, and a microprocessor,
wherein:
the object identifier is configured to read a particular location-identifying object from among the plurality of location-identifying objects;
the internal storage device is configured to store location-specific content; and
the microprocessor is configured to cause the location-specific content to be provided to a child via the smart toy responsive to the object identifier reading the particular location-identifying object from among the plurality of location-identifying objects;

wherein:
the smart toy includes a display screen and a speaker;
the location-specific content includes location-specific viewable content, one or more viewable reminders, location-specific audible content, and one or more audible reminders;
the microprocessor is configured to cause the location-specific viewable content to be displayed on the display screen of the smart toy responsive to the object identifier reading the particular location-identifying object from among the plurality of location-identifying objects;
the microprocessor is configured to cause the location-specific audible content to be emitted via the speaker of the smart toy responsive to the object identifier reading the particular location-identifying object from among the plurality of location-identifying objects;
the microprocessor is configured to cause the one or more viewable reminders to be displayed on the display screen of the smart toy;
the microprocessor is configured to cause the one or more audible reminders to be emitted via the speaker of the smart toy;
the location-specific viewable content includes at least one of an image related to a childhood illness, an instruction related to childhood illness, or information about a medical procedure;
the location-specific audible content includes at least one of an image related to a childhood illness, an instruction related to childhood illness, or information about a medical procedure;
the one or more viewable reminders includes at least one of a reminder about a medical appointment or a reminder about when to take a medication; and
the one or more audible reminders includes at least one of a reminder about the medical appointment or a reminder about when to take the medication.

15. The system of claim 14, wherein:
the particular location-identifying object is referred to as a first particular location-identifying object;
the location-specific content is referred to as first location-specific content;
the object identifier is configured to read a second particular location-identifying object from among the plurality of location-identifying objects;
the internal storage device is configured to store second location-specific content; and
the microprocessor is configured to cause the second location-specific content to be provided to the child via the smart toy responsive to the object identifier reading the second particular location-identifying object from among the plurality of location-identifying objects.

* * * * *